(12) United States Patent
Knappe et al.

(10) Patent No.: US 6,506,575 B1
(45) Date of Patent: Jan. 14, 2003

(54) ANALYTICAL ELEMENT AND METHOD FOR THE DETERMINATION OF AN ANALYTE IN A LIQUID

(75) Inventors: Wolfgang Reinhold Knappe, Ludwigshafen (DE); Rudolf Pachl, Ellerstadt (DE); Otto Gaa, Worms (DE)

(73) Assignee: Roche Diagnostics GmbH, Mannheim (DE)

( * ) Notice: Subject to any disclaimer, the term of this patent is extended or adjusted under 35 U.S.C. 154(b) by 43 days.

(21) Appl. No.: 09/667,931

(22) Filed: Sep. 22, 2000

(30) Foreign Application Priority Data

Sep. 24, 1999 (DE) .......................... 199 45 828

(51) Int. Cl.⁷ .......................... C12Q 1/26; C12Q 1/54; C12M 1/36
(52) U.S. Cl. .......................... 435/25; 435/14; 435/19; 435/283.1; 435/286.5; 435/28; 422/68.1
(58) Field of Search .......................... 435/25, 14, 19, 435/283.1, 286.5, 28

(56) References Cited

U.S. PATENT DOCUMENTS

| | | | | |
|---|---|---|---|---|
| 4,312,834 A | | 1/1982 | Vogel et al. ................. | 422/56 |
| 4,665,023 A | | 5/1987 | Deneke et al. ............... | 435/28 |
| 4,806,312 A | * | 2/1989 | Greenquist .................. | 422/56 |
| 5,206,147 A | | 4/1993 | Hoenes ........................ | 435/25 |
| 5,240,860 A | | 8/1993 | Hoenes et al. ............... | 436/111 |
| 6,036,919 A | | 3/2000 | Thym et al. .................. | 422/58 |

FOREIGN PATENT DOCUMENTS

| | | |
|---|---|---|
| EP | 0 016 387 | 1/1982 |
| EP | 0 161 436 | 5/1987 |
| EP | 0 045 476 | 10/1991 |
| EP | 0 354 441 | 4/1993 |
| EP | 0 431 456 | 8/1993 |
| EP | 0 821 234 | 3/2000 |
| JP | 5 023 199 | 2/1993 |

* cited by examiner

Primary Examiner—Louise N. Leary
(74) Attorney, Agent, or Firm—Jill L. Woodburn; Richard T. Knauer

(57) ABSTRACT

The invention concerns an analytical element for determining the amount of an analyte in a liquid containing a sample application zone (1) and a detection zone (2) which are in liquid-transferring contact, the latter containing at least one enzyme and an indicator substance, the enzyme catalysing a reaction in which the analyte or a substance derived from the analyte participates and the indicator substance forming a signal when the analyte is present which signal correlates with the amount of analyte, and containing a liquid-permeable interference-reducing layer (3) in direct contact with the detection zone (2) arranged such that liquid does not reach the detection zone until it has passed through the interference-reducing layer, the interference-reducing layer containing at least one enzyme which participates in a reaction of the analyte to be determined or of a substance derived from the analyte, wherein the analyte or the substance derived from the analyte is converted enzymatically in the interference-reducing layer into end products which cannot contribute to the signal formation by the indicator substance, and a method for the determination of an analyte in a liquid by means of such an analytical element.

31 Claims, 3 Drawing Sheets

ANALYTICAL ELEMENT AND METHOD FOR THE DETERMINATION OF AN ANALYTE IN A LIQUID

BACKGROUND AND SUMMARY OF THE INVENTION

The application concerns an analytical element for determining the amount of an analyte in a liquid containing a sample application zone and a detection zone which are in liquid-transferring contact, the latter containing at least one enzyme and an indicator substance, the enzyme catalysing a reaction in which the analyte or a substance derived from the analyte participates and the indicator substance forming a signal when the analyte is present which signal correlates with the amount of analyte, and containing a liquid-permeable interference-reducing layer in direct contact with the detection zone arranged such that liquid does not reach the detection zone until it has passed through the interference-reducing layer, the interference-reducing layer containing at least one enzyme which participates in a reaction of the analyte to be determined or of a substance derived from the analyte. The application additionally concerns a method for the determination of an analyte in a liquid by means of such a multilayer analytical element.

Results for analytes to be detected that are too high i.e. false positive often occur with analytical elements of the dry chemistry type which are often called test strips on which undosed sample volumes and hence volumes which vary widely are applied. In addition it is often not possible to recognize when the detection reaction is completed. The detection reaction often slowly declines over a long time period (reaction creep).

The Japanese laid-open specification No. Hei 5-23199 (publication date Feb. 2, 1993) describes an analytical element and a corresponding analytical method for analysing neutral fats. The object of the invention described in the patent application is to remove glycerol that was originally present in the samples to be examined before carrying out an enzymatic analysis of neutral fats via glycerol as an intermediate step. This is achieved by providing analytical elements for the analysis of neutral fats which have at least one reagent layer on a transparent support and a reaction layer thereon. The reaction layer which is the first layer to come into contact with the sample to be examined contains glycerol dehydrogenase and $NAD^+$. The reagent layer also contains glycerol dehydrogenase but no co-enzyme. Consequently glycerol is converted into dihydroxyacetone and NADH in the reaction layer which acts as an interference-reducing layer and is thereby removed. Apparently the $NAD^+$ which diffuses together with the sample from the reaction layer into the reagent layer, activates the glycerol dehydrogenase that is present there such that glycerol formed in the course of the analytical reaction of the neutral fats is also converted in the reagent layer into dihydroxyacetone and NADH. The NADH that is formed reacts with a chromogen in the reagent layer to form a coloured detection product. It is to be expected that NADH which diffuses from the reaction layer into the reagent layer during the course of the analysis would influence the colour reaction in a false-positive manner.

In view of this prior art it was regarded as an object to provide analytical elements which also give correct results with undosed samples i.e. results which agree with those obtained with the respective reference methods. In addition the result should be available after a short time. It should be possible to clearly recognize the end of the detection reaction by the fact that there is no further substantial change in a signal that is used to determine an analyte.

This object is achieved according to the invention by the subject matter which is characterized in more detail in the patent claims.

The invention concerns in particular an analytical element for determining the amount of an analyte in a liquid containing a sample application zone and a detection zone which are in liquid-transferring contact, the latter containing at least one enzyme and an indicator substance, the enzyme catalysing a reaction in which the analyte or a substance derived from the analyte participates and the indicator substance forming a signal when the analyte is present which signal correlates with the amount of analyte, and containing a liquid-permeable interference-reducing layer in direct contact with the detection zone arranged such that liquid does not reach the detection zone until it has passed through the interference-reducing layer, the interference-reducing layer containing at least one enzyme which participates in a reaction of the analyte to be determined or of a substance derived from the analyte, characterised in that the analyte or the substance derived from the analyte is converted enzymatically in the interference-reducing layer into end products which cannot contribute to the signal formation by the indicator substance.

The invention also concerns a method for the determination of an analyte in a liquid by means of an analytical element described above characterised in that liquid is applied to the sample application zone in an undosed manner, liquid passes through the interference-reducing layer into the detection zone and there the amount of analyte in the liquid is determined in this process the detection zone is filled with liquid and excess liquid remains in the interference-reducing layer and optionally in the sample application zone.

A subject matter of the invention is especially the use of a layer in a multilayer analytical element which converts an analyte to be determined or a substance derived therefrom into products which do not contribute to the signal formation in this multilayer analytical element for the determination of this analyte, to prevent rediffusion of analyte from other zones into the zone of the analytical element in which it is intended to detect the analyte when the detection zone is filled with liquid.

An analytical element according to the invention contains a matrix material which contains a sample application zone and a detection zone. Several matrix materials may also be present one of which carries a sample application zone and the other carries the detection zone. All absorbent or swellable materials which can imbibe a liquid can basically be used as matrix materials. These can be fibrous materials such as fleeces, fabrics or knitted fabrics or non-fibrous materials such as porous or non-porous films or membranes.

In an analytical element according to the invention the sample application zone and the detection zone are in a liquid-transfer-enabling contact. The sample application zone can touch the detection zone. However, both zones can also be separate provided that liquid which is applied to the sample application zone can pass into the detection zone in the analytical element.

In order to improve the handling of the analytical element, the sample application zone and the detection zone can be disposed on an inert stiff support material. All inert, adequately stiff materials such as glass, hydrophobised cardboard or polymer materials are potentially suitable for such a support material. Stiff polymer foils which are for example composed of methacrylate/acrylate, polystyrene or polycarbonate are preferably used. In addition the support material can be transparent or impermeable to light.

In an analytical element according to the invention the sample application zone and detection zone can be arranged next to one another or above one another.

The sample application zone refers to the area of the analytical element according to the invention on which the liquid sample is applied. The detection zone of the analytical element according to the invention is understood as the area in which, in the presence of the analyte, a signal is produced which correlates with the amount of the analyte.

The reagents required to determine the amount of an analyte can be distributed over several layers in the detection zone. This has proven to be especially advantageous when certain reagents are not compatible with one another and thus cannot be accommodated within one layer. The detection zone contains at least one enzyme and an indicator substance which, as described above, can both be present within or on a layer or can be located in or on several layers. In this connection an enzyme is understood as a protein which, together with a prosthetic group or a co-enzyme, catalyses a reaction in which the analyte or a substance derived from the analyte participates. In a glucose test the enzyme can for example be glucose oxidase. When detecting triglycerides this enzyme can for example also be glycerokinase which catalyses a reaction of the substance glycerol derived from the analyte triglyceride. Substances derived from the analyte are usually those that have been formed from the substance to be determined by means of an enzymatic or non-enzymatic reaction and whose amount can be correlated with the amount of the analyte.

Indicator substances refer to those materials which produce a signal with a substance derived from the analyte which correlates with the amount of analyte. Suitable indicator substances according to the invention are in particular those which produce a colour, lose their colour or change their colour or which lose fluorescence or generate fluorescence in the presence of the analyte when the analytical element according to the invention is used. However, those indicator substances are preferred according to the invention which produce a colour, lose their colour or change their colour. Such substances are also referred to as chromogens.

The analytical element according to the invention contains a liquid-permeable interference-reducing layer in direct contact with the detection zone. The interference-reducing layer is arranged such that liquid only reaches the detection zone after passing through the interference-reducing layer. In this connection the interference-reducing layer and detection zone can be arranged next to one another or above one another. The interference-reducing layer can represent the sample application zone when liquid sample is applied directly to the interference-reducing layer. The interference-reducing layer and sample application zone can, however, also be spatially separate from one another. Thus the sample application zone and interference-reducing layer can also be stacked on top of one another or be arranged next to one another if the sample application zone and interference-reducing layer are not identical.

According to the invention the interference-reducing layer contains at least one enzyme which catalyses a. reaction of the analyte to be determined or of a substance derived from the analyte to obtain end products which cannot contribute to the signal generation by the indicator substance. Consequently end products are obtained according to the invention in the interference-reducing layer from the analyte or from a substance derived from the analyte at the end of the enzymatic interference-reducing reaction which cannot generate a signal with the indicator substance. If for example the indicator substance together with hydrogen peroxide forms a dye in the presence of peroxidase, then the analyte or the substance derived from the analyte must be enzymatically converted in the interference-reducing layer in such a manner that ultimately no hydrogen peroxide remains in the interference-reducing layer. Should hydrogen peroxide be formed enzymatically in the interference-reducing layer, this must be enzymatically reacted further in the interference-reducing layer such that hydrogen peroxide does not remain in the interference-reducing layer as an end product. For example a reaction producing hydrogen peroxide can be coupled with a reaction consuming hydrogen peroxide. Catalase or peroxidase can be used for this as proteins that decompose hydrogen peroxide.

If an indicator substance is used in the detection zone which is accepted instead of oxygen as the electron-accepting substance by redox enzymes such as oxidases, it is possible to place a hydrogen peroxide producing reaction system in the interference-reducing layer. Substances which are accepted by redox enzymes as electron-accepting substances instead of oxygen are for example described in the European Patent Application 0 354 441. Such substances are not influenced further by hydrogen peroxide.

If a chromogen is used as the indicator substance, it is obvious that those end products are formed in the interference-reducing layer which do not interfere with the colour formation or colour change of the indicator substance. If the indicator substance forms a colour in the presence of the analyte, it is advantageous when the end products formed in the interference-reducing layer are colourless.

If a co-enzyme-dependent enzyme is used in the enzyme-containing layer of the detection zone, the required co-enzyme is preferably located in the analytical element according to the invention in the same layer of the detection zone.

Whereas the reagents required to determine the analyte can be separated into several layers of the detection zone as described above, it has proven to be particularly advantageous when the interference-reducing layer and a layer of the detection zone containing enzyme and indicator substance are arranged to be in direct contact with one another in the analytical element according to the invention. Under certain circumstances the substances required to determine the analyte that are not accommodated in the same layer of the detection zone containing the enzyme and/or indicator substance can also be located in the interference-reducing layer.

As already mentioned above the interference-reducing layer can also be the sample application zone if liquid sample is applied directly to the interference-reducing layer. However, it may also be expedient to not directly apply the sample to be determined to the interference-reducing layer but rather to a sample application zone that is located in front of the interference-reducing layer. This may then be particularly advantageous when for example it is intended to examine liquids containing particles such as blood. In such cases it has proven to be preferable to separate and retain the particles that are present in the liquid, such as blood cells like erythrocytes, in the sample application zone before the remaining liquid passes into the interference-reducing layer. In such cases it has proven to be advantageous to use fibrous matrix materials and especially fleeces and very preferably glass fibre fleeces as described for example in the European Patent Application 0 045 476.

In a determination method according to the invention an analytical element as described above is used. Liquid is preferably applied unmetered to the sample application zone. This is possible when a matrix material is used as the detection zone which can imbibe an exactly defined liquid volume. Such materials are known to a person skilled in the art. For example membranes are commercially available which fulfil these conditions. Films can, however, also be used as known for example from the European Patent Application 0 016 387.

Liquid passes from the sample application zone through the interference-reducing layer into the detection zone where the indicator substance produces a signal when the analyte is present which correlates with the amount of analyte. The signal can be measured by an apparatus. In the case of colour formation, colour reduction or colour change the signal can be measured by an instrument e.g. by reflection photometry or it can be determined visually.

The method according to the invention for the determination of an analyte in a liquid by means of an analytical element according to the invention can be carried out advantageously especially when so much liquid has been applied to the sample application zone of the analytical element that excess liquid remains in the interference-reducing layer and optionally in the sample application zone. In such cases false-positive results are often obtained with analytical elements of the prior art or the end of the signal generating reaction is not clearly discernible because analyte rediffuses from the excess liquid into the detection zone. In contrast the method according to the invention and the analytical element according to the invention can be particularly advantageously employed when using undosed liquid samples since falsely elevated results are not found and the end of the detection reaction can be clearly recognized since after a certain time point there is no further significant change in signal. Results are obtained with the method according to the invention and analytical element according to the invention which correlate well with those of standard wet chemistry methods. This applies in particular to the determination of trigylcerides and glucose.

The advantages of the analytical element according to the invention and of the method according to the invention are primarily achieved by using a layer in a multilayer analytical element which converts an analyte to be determined or a substance derived therefrom into products which do not contribute to the signal generation in the multilayer analytical element. This prevents rediffusion of analyte from other zones into the zone of the analytical element in which the detection of the analyte is to take place. This effect occurs in particular when the detection zone is filled with liquid and excess liquid is still present in other zones of the analytical element.

DETAILED DESCRIPTION OF THE INVENTION

Advantageous embodiments of the analytical element according to the invention are shown in FIGS. 1–5. FIG. 6 shows the reaction time course (measured in % reflection versus time in seconds) in various analytical elements in one graph.

Figure 1:
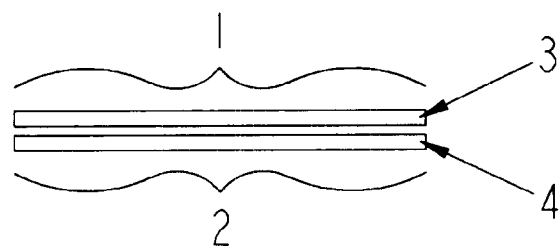
FIG. 1 shows an analytical element according to the invention in which a sample application zone and a detection zone are stacked on top of one another.

FIG. 1 shows an analytical element according to the invention in which the sample application zone (1) and detection zone (2) are stacked on top of one another. The interference-reducing layer (3) is located in the sample application zone (1). The layer (4) containing the indicator substance is located in the detection zone (2).

Figure 2:
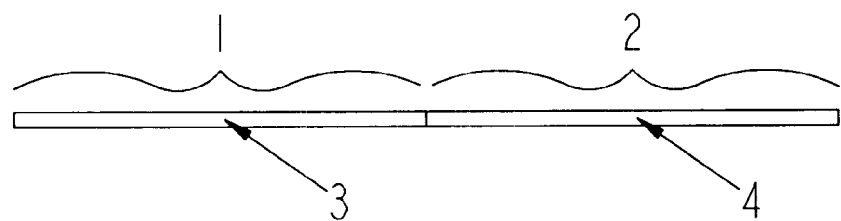
FIG. 2 shows an analytical element according to the invention in which a sample application zone and a detection zone are located next to one another.

FIG. 2 shows an analytical element according to the invention in which the sample application zone (1) and detection zone (2) are located next to one another. In this case the interference-reducing layer (3) is also located in the sample application zone (1). The layer (4) containing the indicator substance is located in the detection zone (2). In the analytical element of FIG. 2 the interference-reducing layer (3) and the layer (4) containing the indicator substance are in contact with one another via their edges. In order to ensure liquid transfer between the two layers, it is also possible to slightly overlap the layers.

Whereas it is advantageous to measure from the detection zone i.e. the side opposite to the sample application zone of an analytical element according to FIG. 1, it is in principle possible to measure signal generation in the detection zone of an analytical element according to FIG. 2 from the same side as the sample application side or from the side of the detection zone opposite to the sample application side. If the layers (3,4) are attached to an inert support material to improve handling, this can only be accomplished in the latter case when the inert support material is transparent or has an opening at least in the area of the detection zone such that the layer (4) containing the indicator substance is freely visible.

Figure 3:
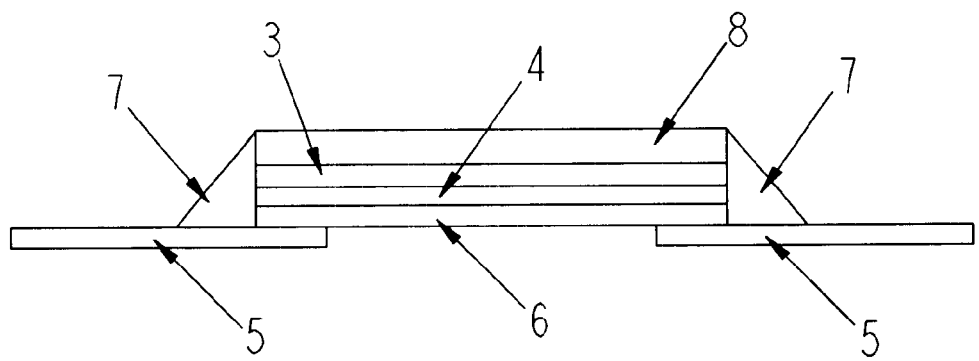
FIG. 3 shows an analytical element according to the invention in which a multilayer stacked construction is attached to a support material.

A preferred analytical element according to the invention is shown in FIG. 3. In this analytical element a multilayer stacked construction is attached to a support material (5) for example by means of hot-melt adhesive (7). A foil (6) which should be light-permeable is located on the support material (5) which can be transparent or impermeable to light. A transparent polycarbonate foil is for example particularly suitable for this. A layer (4) containing indicator substance, above it an interference-reducing layer (3) and a particle-retaining layer (8) as the uppermost layer are arranged on this foil (6). The transparent foil (6) and the overlying layer (4) containing indicator substance are visible through an opening in the support material (5).

The structure of such an analytical element is particularly suitable for determining an analyte in whole blood. A fibrous layer, in particular a glass fibre fleece as described in the European Patent Application No. 0 045 476 has proven to be particularly advantageous for layer (8) in order for it to retain erythrocytes as particles contained in whole blood. Multifilament fabrics or fleeces such as paper or silk fabric have proven to be particularly preferable for the interference-reducing layer (3). A porous membrane is well-suited for the underlying layer (4) containing the indicator substance. However, films have proven to be particularly advantageous as described for example in the European Patent Application No. 0 016 387 which incorporate the indicator substance as well as the required reagents such as the necessary enzyme. Such films can be produced directly on a transparent foil such as a polycarbonate foil that is used preferably as the foil (6) in the analytical element according to the invention. The interference-reducing layer (3) can particularly advantageously contain the necessary substances in an impregnated form in the case of a multifilament fabric or fleece. However, it is alternatively also possible that a film is applied as described above onto a foil (6) as the layer (4) containing the indicator substance and an additional film is applied thereto as an interference-reducing layer (3) in a further coating process.

An analytical element as shown in FIG. 3 is well suited for the determination of the amount of triglyceride in blood in which the following enzymatic reactions occur:

The analytical element according to the invention as shown in FIG. 3 can also be used very well for the determination of glucose in blood. In this case glucose oxidase and a substance which can transfer electrons instead of oxygen from the redox enzyme to an indicator substance which is also located in layer (4) are present in layer (4) containing the indicator substance. Such reaction systems are for example known from the European Patent Application No. 0 431 456. Glucose oxidase can for example be present in an interference-reducing layer located above layer (4). Thus when layer (4) is filled with liquid, glucose is converted by means of glucose oxidase to $H_2O_2$ in the liquid above which no longer interferes with the indicator system that is present in the underlying layer (4). Thus for example an analytical element for the determination of glucose can be produced which reaches a reaction end within a short time and does not have a reaction creep.

Figure 4:
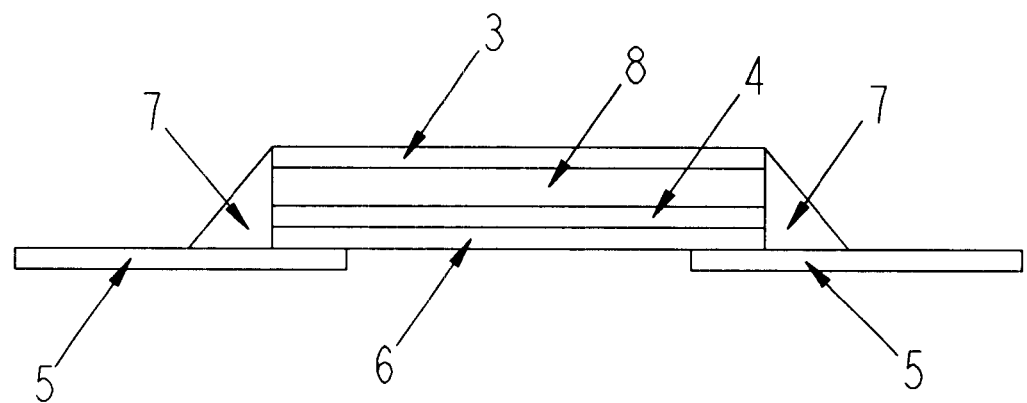
FIG. 4 shows an analytical element according to the invention in which, compared to the element of FIG. 3, the order of layers are interchanged.

FIG. 4 shows an analytical element according to the invention in which, compared to the element of FIG. 3, the order of the layers (8) and (3) is interchanged. In this case the sample firstly reaches the interference-reducing layer (3) and undergoes reactions there before the liquid migrating

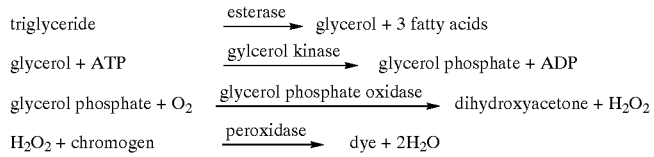

triglyceride $\xrightarrow{\text{esterase}}$ glycerol + 3 fatty acids glycerol + ATP $\xrightarrow{\text{gylcerol kinase}}$ glycerol phosphate + ADP glycerol phosphate + $O_2$ $\xrightarrow{\text{glycerol phosphate oxidase}}$ dihydroxyacetone + $H_2O_2$ $H_2O_2$ + chromogen $\xrightarrow{\text{peroxidase}}$ dye + $2H_2O$ A chromogen which forms a dye in the presence of peroxidase and $H_2O_2$ is located in the layer (4) containing indicator substance. Diarylimidazoles can for example be used in this case as the chromogen which are known from the European Patent Application 0 161 436. Glycerol kinase and glycerol phosphate oxidase in addition to ATP are also located in the layer (4) containing the indicator substance and are used to enzymatically convert glycerol in the presence of atmospheric oxygen into $H_2O_2$ which can then form a colour signal with the chromogen. Glycerol is a substance derived from the analyte triglyceride to be determined and is produced from triglyceride by the esterase. The amount of glycerol and ultimately the amount of $H_2O_2$ correlates with the amount of originally present triglyceride in the sample. However, free glycerol is also present in blood samples that are to be examined for triglyceride. If an undosed blood volume is applied to the particle-retaining layer (8) of the analytical element according to FIG. 3 in such a manner that the layer (4) containing indicator substance is saturated with liquid and an excess of liquid remains in the overlying layer, there would be a risk that during the course of time required for the determination reaction free glycerol that is present there would rediffuse into the layer (4) containing the indicator substance and would also lead to a colour signal via the described enzymatic reactions which would ultimately simulate a higher value for triglyceride than is actually present. This rediffusion of free glycerol from the layers arranged above the layer (4) containing indicator substance is prevented by placing the enzymes glycerol kinase, glycerol phosphate oxidase, peroxidase and ATP in the interference-reducing layer (3) which degrades glycerol via dihydroxyacetone and $H_2O_2$ to dihydroxyacetone and water. As a result substances are produced which cannot contribute to the signal generation by the indicator substance. The triglyceride values that are obtained in this manner agree very well with reference methods.

through the layers reaches and penetrates the particle-retaining layer (8).

Figure 5:
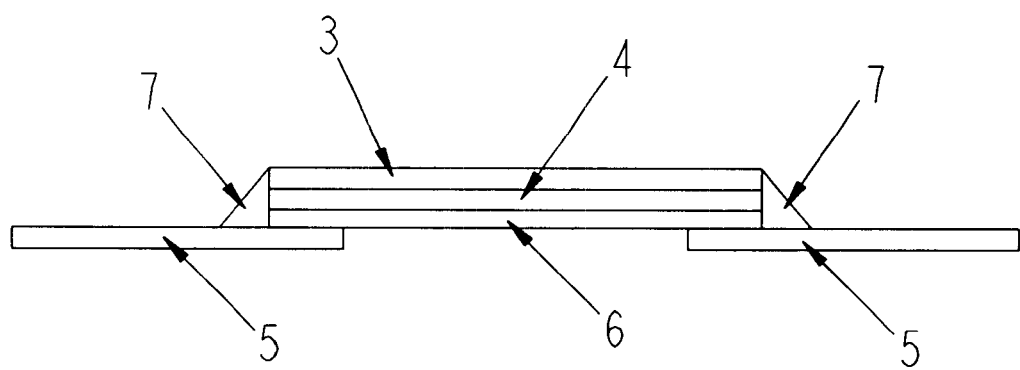
FIG. 5 shows an analytical element according to the invention in which an interference-reducing layer has the function of erythrocyte separation.
Figure 6:
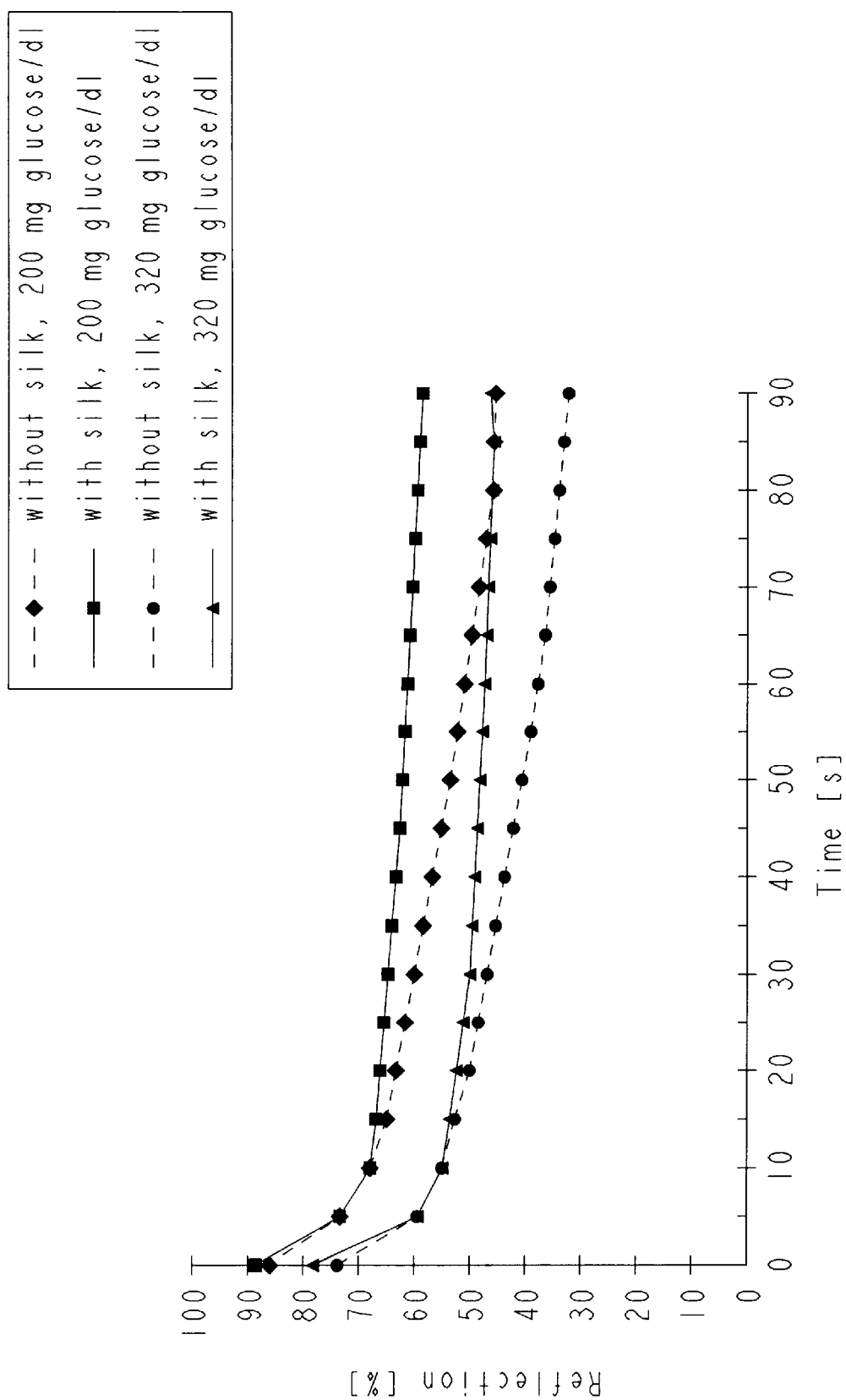
FIG. 6 is a graph showing the reaction time course in various analytical elements.

A further preferred analytical element according to the invention is shown in FIG. 5. In comparison to the analytical elements of FIGS. 3 and 4 this analytical element requires no extra layer (8) which retains particles such as erythrocytes from the sample. In this case the interference-reducing layer (3) additionally has the function of erythrocyte separation.

The interference-reducing layer (3) and layer (4) containing indicator substance can be designed as films that are coated on top of one another as for example known from EP-A 0 821 234.

The invention is elucidated in more detail in the following examples.

EXAMPLE 1

Analytical Element for the Determination of Triglyceride According to FIG. 3

Layer Containing Indicator Substance

A reagent composition comprising 67.0 g water 0.14 g potassium hydrogen phosphate 1.15 g di-sodium hydrogen phosphate dihydrate 2.0 g copolymer of methylvinylether and maleic acid (Gantrez S 97)

4.5 g sodium hydroxide 0.8 g wetting agent TRITON®X100

0.5 g wetting agent (dioctylsodium sulfosuccinate) in 2.1 g acetone 1.7 g titanium dioxide 15.0 g kieselguhr 6.6 g 50% polyvinylpropionate dispersion (Propiofan 70D from BASF, Ludwigshafen, Germany)

0.6 g magnesium sulphate heptahydrate 0.7 g 2-(3,5-dimethoxy-4-hydroxyphenyl)-4(5)-(4-dimethylaminophenyl)-5(4)-methyl-(1H)-imidazole-dihydrochloride (EP-A-0 161 436)

9.5 kU peroxidase (from horseradish)

13.0 kU cholesterol esterase 15.0 kU glycerol kinase 6.2 kU glycerol phosphate oxidase 10 mg 1-(4-methylphenyl)-semicarbazide in 0.25 g 1-methoxy-2-propanol is coated at a thickness of 0.2 mm on a polycarbonate foil (layer (6) according to FIG. 3) and dried for 40 minutes at 50° C. From this strips of 6 mm width are cut and incorporated as a reagent film (layer (4) containing indicator substance) into test strips according to FIG. 3.

Interference-reducing Layer

An impregnation solution composed of 2500.0 g water 0.95 g potassium dihydrogen phosphate 37.4 g di-sodium hydrogen phosphate dihydrate 26.0 g di-sodium adenosine-5'-triphosphate trihydrate 26.0 g magnesium sulphate heptahydrate 1.6 MU glycerol kinase 1.2 MU glycerol phosphate oxidase 21.0 MU peroxidase is used to impregnate silk fabric (type 541 from the Spinnhütte Company, Celle, Germany) or stencil paper (15 g/m² from the Schöller Company, Germany) and dried for 30 minutes at 50° C.

From this strips of 6 mm width are cut and incorporated as an interference-reducing layer (3) into the test strips of FIG. 3.

White pigmented polyester foil of 0.35 mm thickness from the Pütz-Folien Company, Taunusstein-Wehen, Germany was used as the support foil (layer (5) according to FIG. 3).

A 6 mm wide glass fibre fleece as described in the examples of EP-A 0 045 476 was attached above the interference-reducing layer as an erythrocyte-retaining layer (8).

In the following EDTA venous blood (native TG content 93 mg/dl, native glycerol content unknown) to which 2, 4, 8 and 16 mg glycerol/dl was successively added was applied to 4 test strip constructions:

a) Analytical element with the above test composition without an interference-reducing layer: Addition of 2 mg glycerol/dl already resulted in a false-positive signal of 74% (the expected increase of 2 mg glycerol=17 mg triglyceride (TG) was taken into account). Further addition of glycerol increases the false-positive signal; the decrease when 16 mg glycerol/dl is added is due to the fact that the end of the measuring range of the NW-TG strip has been reached (the test strip is "titrated out").

b) Test strips with the above test composition containing an interference-reducing layer of stencil paper (buffer paper) which was only impregnated with buffer: Same effect as without this paper. Test strips in which silk impregnated with buffer was inserted also showed the same effect.

c) Test strips with the above test composition containing an interference-reducing layer of stencil paper (enzyme paper) which was impregnated with the above impregnation solution: In this case the additions of glycerol only resulted in false-positive readings of 11 to 33% (the same reduction of interference was observed with an impregnated paper which contained catalase instead of POD).

d) Test strips with the above test composition containing an interference-reducing layer of silk (enzyme silk) which was impregnated with the above impregnation solution: In this case the additions of glycerol only led to false-positive readings of 4 to 29%. (Also in this case the same reduction of interference was observed with an impregnated silk which contained catalase instead of POD).

TABLE 1

| Blood with added glycerol | | | | | |
|---|---|---|---|---|---|
| glycerol addition (mg/dl) | 0 | 2 | 4 | 8 | 16 |
| =TG equivalent | 0 | 17 | 34 | 68 | 136 |
| expected value (reference): | 93 | 110 | 127 | 161 | 229 |
| a) without interference-reducing layer | 129 | 254 | 385 | 662 | 759 |
| b) with buffer paper | 133 | 293 | 470 | 589 | 633 |
| c) with enzyme paper | 94 | 123 | 143 | 215 | 306 |
| d) with enzyme silk | 119 | 144 | 160 | 211 | 329 |

| | Relative deviation when glycerol is added | | | |
|---|---|---|---|---|
| | 2 mg/dl | 4 mg/dl | 8 mg/dl | 16 mg/dl |
| without interference-reducing layer | 74% | 136% | 236% | 186% |
| with buffer paper | 95% | 182% | 193% | 135% |
| with enzyme paper | 11% | 12% | 33% | 33% |
| with enzyme silk | 6% | 4% | 13% | 29% |

The relative deviations relate to a calculated expected value which results from adding the measured triglyceride concentration with no addition of glycerol and the triglyceride (TG) equivalents of the glycerol addition. In the case of the 4 mg/dl glycerol addition it therefore gives the following calculation for the relative deviation for the enzyme paper:

$$(143-\{94+34\}):(94+34)=12\%$$

EXAMPLE 2

Rediffusion of Glycerol in Analytical Elements for the Determination of Triglyceride In order to prove that the rediffusion of glycerol is the cause for a false-positive reaction, human serum with triglyceride concentrations of 5 and 150 mg/dl without and with glycerol additions of 5 mg/dl were spotted (20 µl) on the following test strip constructions:

a) test strip No. 1 with the above test composition according to example 1 and FIG. 3 without an interference-reducing layer.

b) test strip No. 2 analogous to FIG. 3 and example 1 but without an interference-reducing layer and without a glass fibre fleece.

c) test strip No. 3 with a test composition according to example 1 and FIG. 3 containing an interference-reducing layer of silk which had been impregnated with the impregnation solution as described in example 1 and measured after 2 min in a reflection photometer. Test strip No. 2 without an interference-reducing layer and without a glass fibre fleece was dabbed dry with a cotton fleece 5 seconds after the spotting. The triglyceride concentrations (1 mg glycerol corresponds to 9.62 mg triolein) summarised in the following table were found by conversion using a function curve:

| TG [mg/dl] | glycerol [mg/dl] | sum [mg/dl] | found concentrations | | |
|---|---|---|---|---|---|
| | | | No.1 [mg TG/dl] | No.2 [mg TG/dl] | No.3 [mg TG/dl] |
| 5 | 0 | 5 | 10 | 0 | 10 |
| 5 | 5 | 53 | 120 | 45 | 55 |
| 150 | 0 | 150 | 150 | 130 | 155 |
| 150 | 5 | 198 | 240 | 175 | 200 |

These values show the following:

Test strip No. 1 without an interference-reducing layer measures false-positively when glycerol is added and strongly false-positively at a low triglyceride concentration:+126% at 5 mg TG/dl,+21% at 198 mg TG/dl.

Test strip No. 2 shows only a slight false-negative deviation.

Test strip No. 3 containing an interference-reducing layer measures correctly.

Summary: In test strip No. 1 glycerol from the supernatant sample rediffuses and results in false-positive values. In the case of test strip No. 2 supernatant is no longer present; the slight false-negative deviations can be explained by the fact that the reaction film was not completely soaked before being dabbed dry. In the case of test strip No. 3 the glycerol of the supernatant is enzymatically converted in the silk fabric lying directly above the reaction film and can therefore not diffuse into the reaction film.

All test strips measure the sum of triglyceride and glycerol which is also the case for the usual reference methods of clinical chemistry.

EXAMPLE 3
Analytical Element for the Determination of Glucose
A reagent composition composed of
1500 g 0.1 M sodium citrate buffer, pH 6.2
46.0 g polyvinylpyrrolidone 25000
16.0 g tetraethylammonium chloride
11.2 g polyxanthan rubber (Keltrol F from the Kelco International Company, Hamburg, Germany), dissolved in 780 g water
15.3 g N-dodecyl-N,N-dimethyl-3-ammonio-1-propane sulphonate
72.0 g sodium-2,18-phosphomolybdate in 108 g water
116.1 g 50% polyvinylpropionate dispersion (Propiofan 70 D from the BASF, Ludwigshafen, Germany)
2.5 g 4-Bis-(2-hydroxyethyl)-amino-nitrosobenzene hydrochloride (EP-A-0 354 441) in 75 g water
8.8 MU glucose oxidase in 235 g water,
is coated at a thickness of 0.12 mm on a polycarbonate foil and dried for 20 minutes at 50° C.

Afterwards this coated foil is recoated with the following reagent composition composed of
1645 g 0.05 M sodium citrate buffer, pH 6.2
116.0 g titanium dioxide
29.7 g polyvinylpyrrolidone 25000
10.2 g tetraethylammonium chloride
13.1 g polyxanthan rubber (Keltrol F from the Kelco International Company, Hamburg, Germany), dissolved in 760 g water
9.9 g N-dodecyl-N,N-dimethyl-3-ammonio-1-propane sulphonate
46.4 g sodium-2,18-phosphomolybdate in 93 g water
74.7 g 50% polyvinylpropionate dispersion (Propiofan 70 D from BASF, Ludwigshafen, Germany)
5.3 MU glucose oxidase in 150 g water
at a thickness of 0.12 mm and dried for 30 min at 50° C.

Strips of 6 mm width are cut from this and incorporated as a reagent film containing indicator substance into test strips according to FIG. 3 which, however, contains no interference-reducing layer. A 6 mm wide glass fibre fleece as described in the examples of EP-A 0 045 476 is attached above the film as an erythrocyte retaining layer.

After application of a solution containing glucose, the reaction time of this glucose test strip which contains no interference-reducing layer is still not completed for whole blood even after 90 seconds as shown in FIG. 6.

Therefore a silk fabric (type 541 from the Spinnhütte Company, Celle, Germany) which was impregnated with an impregnation solution composed of
50 g sodium citrate buffer pH 6.0
130 kU glucose oxidase
was incorporated according to FIG. 3 into the test strip between the glass fibre fleece and the film containing the indicator substance and dried for 30 minutes at 50° C.

After application of a solution containing glucose the colour development in this test strip is now completed after 30 seconds (see FIG. 6).

What is claimed is:

1. Analytical element for determining the amount of an analyte in a liquid, the element comprising a sample application zone and a detection zone which are in liquid-transferring contact, the detection zone containing at least one enzyme and an indicator substance, the enzyme catalysing a reaction in which the analyte or a substance derived from the analyte participates and the indicator substance forming a signal when the analyte is present which signal correlates with the amount of analyte, and a liquid-permeable interference-reducing layer in direct contact with the detection zone arranged such that liquid does not reach the detection zone until the liquid has passed through the interference-reducing layer, the interference-reducing layer containing at least one enzyme which participates in a reaction of the analyte to be determined or of a substance derived from the analyte, wherein the analyte or the substance derived from the analyte is converted enzymatically in the interference-reducing layer into end products which cannot contribute to the signal formation by the indicator substance.

2. Analytical element as claimed in claim 1, wherein the interference-reducing layer and detection zone are arranged above one another.

3. Analytical element as claimed in 2, wherein the interference-reducing layer and the layer of the detection zone containing enzyme and indicator substance are arranged in direct contact with one another.

4. Analytical element as claimed in 1, wherein the interference-reducing layer and the layer of the detection zone containing enzyme and indicator substance are arranged in direct contact with one another.

5. Analytical element as claimed in claim 1, wherein a layer is located in the sample application zone that retains particles contained in the liquid.

6. Analytical element as claimed in claim 2, wherein a layer is located in the sample application zone that retains particles contained in the liquid.

7. Analytical element as claimed in claim 4, wherein a layer is located in the sample application zone that retains particles contained in the liquid.

8. Analytical element as claimed in 1, wherein the interference-reducing layer is in the sample application zone.

9. Analytical element as claimed in 2, wherein the interference-reducing layer is in the sample application zone.

10. Analytical element as claimed in 4, wherein the interference-reducing layer is in the sample application zone.

11. Analytical element as claimed in claim 1, wherein the end product formed in the interference-reducing layer is colorless.

12. Analytical element as claimed in claim 2, wherein the end product formed in the interference-reducing layer is colorless.

13. Analytical element as claimed in claim 4, wherein the end product formed in the interference-reducing layer is colorless.

14. Analytical element as claimed in claim 5, wherein the end product formed in the interference-reducing layer is colorless.

15. Analytical element as claimed in claim 8, wherein the end product formed in the interference-reducing layer is colorless.

16. Analytical element as claimed in claim 1, wherein the layer of the detection zone containing enzyme contains the necessary coenzyme if the enzyme of the detection layer is coenzyme-dependent.

17. Analytical element as claimed in claim 2, wherein the layer of the detection zone containing enzyme contains the necessary coenzyme if the enzyme of the detection layer is coenzyme-dependent.

18. Analytical element as claimed in claim 4, wherein the layer of the detection zone containing enzyme contains the necessary coenzyme if the enzyme of the detection layer is coenzyme-dependent.

19. Analytical element as claimed in claim 5, wherein the layer of the detection zone containing enzyme contains the necessary coenzyme if the enzyme of the detection layer is coenzyme-dependent.

20. Analytical element as claimed in claim 8, wherein the layer of the detection zone containing enzyme contains the necessary coenzyme if the enzyme of the detection layer is coenzyme-dependent.

21. Analytical element as claimed in claim 11, wherein the layer of the detection zone containing enzyme contains the necessary coenzyme if the enzyme of the detection layer is coenzyme-dependent.

22. A method for the determination of an analyte in a liquid, the method comprising the steps of:

provforming a multilayer analytical element comprising a sample application zone, a detection zone in liquid-transferring contact with the sample application zone, the detection zone containing at least one enzyme and an indicator substance, and a liquid-permeable interference-reducing layer in direct contact with the detection zone arranged such that liquid does not reach the detection zone until the liquid has passed through the interference-reducing layer, the interference-reducing layer containing at least one enzyme which participates in a reaction of the analyte to be determined or of a substance derived from the analyte, applying the liquid to the sample application zone in an undosed manner so that the liquid passes through the interference-reducing layer into the detection zone and fills the detection zone where the enzyme catalyzes a reaction in which the analyte or a substance derived from the analyte participates and forms a signal when the analyte is present which signal correlates with the amount of analyte present in the liquid and excess liquid remains in the interference-reducing layer is exposed to the at least one enzyme which enzymatically converts the analyte or the substance derived from the analyte into end products which cannot contribute to the signal formation by the indicator substance, and determining the amount of analyte in the liquid.

23. The method of claim 22 wherein the applying step includes filling the detection zone with liquid so that excess liquid remains in the application zone.

24. Method as claimed in claim 22, wherein the liquid to be examined at least partially passes through the interference-reducing layer before the enzyme of the interference-reducing layer begins to act.

25. Analytical element as claimed in claim 1, wherein the signal generated by the indicator substance in the presence of the analyte is a color change.

26. Analytical element as claimed in claim 25, wherein the interference-reducing layer and detection zone are arranged above one another.

27. Analytical element as claimed in claim 25, wherein the interference-reducing layer and the layer of the detection zone containing enzyme and indicator substance are arranged in direct contact with one another.

28. Analytical element as claimed in claim 25, wherein the interference-reducing layer is in the sample application zone.

29. Analytical element as claimed in claim 25, wherein the end product formed in the interference-reducing layer is colorless.

30. Analytical element as claimed in claim 25, wherein the layer of the detection zone containing enzyme contains the necessary coenzyme if the enzyme of the detection layer is coenzyme-dependent.

31. Analytical element as claimed in claim 25, wherein a layer is located in the sample application zone that retains particles contained in the liquid.

* * * * *